United States Patent
Nanjo

(10) Patent No.: US 12,076,176 B2
(45) Date of Patent: Sep. 3, 2024

(54) DYNAMIC IMAGE PROCESSING APPARATUS AND STORAGE MEDIUM

(71) Applicant: Konica Minolta, Inc., Tokyo (JP)

(72) Inventor: Takafumi Nanjo, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 517 days.

(21) Appl. No.: 17/333,617

(22) Filed: May 28, 2021

(65) Prior Publication Data
US 2021/0369225 A1 Dec. 2, 2021

(30) Foreign Application Priority Data
May 28, 2020 (JP) .................. 2020-092799

(51) Int. Cl.
*A61B 6/00* (2024.01)
*A61B 6/46* (2024.01)
*G06T 3/4053* (2024.01)
*G16H 30/40* (2018.01)

(52) U.S. Cl.
CPC ............ *A61B 6/5211* (2013.01); *A61B 6/463* (2013.01); *A61B 6/486* (2013.01); *G06T 3/4053* (2013.01); *G16H 30/40* (2018.01)

(58) Field of Classification Search
CPC ....... A61B 6/463; A61B 6/486; A61B 6/5211; G06T 3/4053; G16H 30/40
See application file for complete search history.

(56) References Cited

U.S. PATENT DOCUMENTS

2012/0130238 A1* 5/2012 Muraoka .............. A61B 6/4233
600/436

FOREIGN PATENT DOCUMENTS

| JP | H0838433 A | 2/1996 |
|---|---|---|
| JP | 2003018541 A | 1/2003 |
| JP | 2005007061 | * 1/2005 |
| JP | 2005287750 A | 10/2005 |
| JP | 2011110211 | * 6/2011 |
| JP | 2015100424 | * 6/2015 |
| JP | 2015100424 A | 6/2015 |
| JP | 2015150206 A | 8/2015 |

(Continued)

OTHER PUBLICATIONS

A machine translated English version of JP 2011110211. (Year: 2011).*

(Continued)

*Primary Examiner* — Ruiping Li
(74) *Attorney, Agent, or Firm* — CANTOR COLBURN LLP

(57) ABSTRACT

A dynamic image processing apparatus processes image data of a medical dynamic image that includes a plurality of frame images obtained from successively imaging a subject and that shows a dynamic state of the subject. The dynamic image processing apparatus includes a hardware processor. The hardware processor enhances resolution of at least one or more of the plurality of frame images included in the medical dynamic image to a high resolution and generates a secondary medical image. The hardware processor executes a recording process in which a record is kept to show that the secondary medical image is generated secondarily from the existing medical dynamic image.

14 Claims, 10 Drawing Sheets

(56) References Cited

FOREIGN PATENT DOCUMENTS

| JP | 2017225475 A | 12/2017 |
|---|---|---|
| JP | 2019212138 A | 12/2019 |

OTHER PUBLICATIONS

A machine translated English version of JP 2005007061 (Year: 2005).*
A machine translated English version of JP2015100424. (Year: 2015).*
JPO Notice of Reasons for Refusal for corresponding JP Application No. 2020-092799; Mailing Date, Aug. 15, 2023.

* cited by examiner

DYNAMIC IMAGE PROCESSING APPARATUS AND STORAGE MEDIUM

CROSS-REFERENCE TO RELATED APPLICATIONS

The present invention claims priority under 35 U.S.C. § 119 to Japanese Patent Application No 2020-092799 filed on May 28, 2020, the entire content of which is incorporated herein by reference.

BACKGROUND

Technological Field

The present invention relates to a dynamic image processing apparatus and a storage medium.

Description of the Related Art

Instead of the conventional imaging of still images by radiation (X-ray) using film/screen or stimulable phosphor plate and using such image in diagnosis, lately, an attempt is made to perform dynamic imaging of a site which is a target of diagnosis (hereinafter referred to as target site) using a semiconductor image sensor such as a FPD (flat panel detector), and applying the result to diagnosis (for example, JP2017-225475).

Specifically, the quickness of the response of the semiconductor image sensor when the image data is read and deleted is used. The pulsed radiation is emitted successively from the radiation source matched with the timing of reading and deleting of the semiconductor image sensor and the imaging is performed a plurality of times in one second. With this, the medical dynamic image including a plurality of frame images is generated. By sequentially displaying on the screen a series of a plurality of frame images included in the medical dynamic image, the doctor is able to observe the string of movement in the target site.

Each of the plurality of frame images included in the medical dynamic image is one individual still image. Therefore, by duplicating one of the plurality of frame images or duplicating and processing the frame image, it is possible to generate a secondary medical image.

SUMMARY

However, the plurality of frame images included in the medical dynamic image are generated for the purpose of being successively displayed to be used for diagnosis of the dynamic state. Therefore, if the secondary medical image is used alone when interpreting the image in medical practice, there is a problem that this may lead to medical problems such as misdiagnosis.

The purpose of the present invention is to provide a dynamic image processing apparatus and a storage medium which can prevent medical problems from occurring.

To achieve at least one of the abovementioned objects, according to an aspect of the present invention, a dynamic image processing apparatus reflecting one aspect of the present invention processes image data of a medical dynamic image that includes a plurality of frame images obtained from successively imaging a subject and that shows a dynamic state of the subject, the apparatus includes a hardware processor, wherein the hardware processor enhances resolution of at least one or more of the plurality of frame images included in the medical dynamic image to a high resolution and generates a secondary medical image, and the hardware processor executes a recording process in which a record is kept to show that the secondary medical image is generated secondarily from the existing medical dynamic image.

According to another aspect, a non-transitory computer-readable storage medium storing a program causing a computer provided in a dynamic image processing apparatus that processes image data of a medical dynamic image that includes a plurality of frame images obtained by successively imaging a subject and that shows a dynamic state of the subject to perform the following: generating a secondary medical image by enhancing a resolution of at least one or more of the plurality of frame images included in the medical dynamic image, and executing a recording process to keep a record showing that the secondary medical image is generated secondarily from the existing medical dynamic image.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Embodiments of a dynamic image processing apparatus and a storage medium are described below. The present invention is not limited to the illustrated examples.

Hereinafter, one or more embodiments of the present invention will be described with reference to the drawings. However, the scope of the invention is not limited to the disclosed embodiments.

Figure 1:
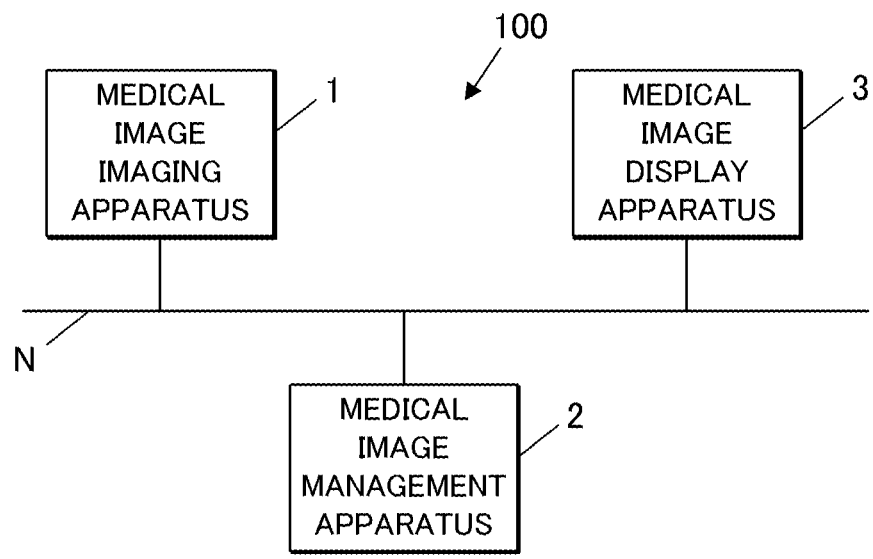
FIG. 1 is a diagram showing an example of a system configuration of a medical information management system.

FIG. 1 is a diagram showing an example of a system configuration of a medical information management system 100.

The medical information management system 100 is a system provided in a medical facility such as a hospital.

As shown in FIG. 1, the medical information management system 100 includes a medical image imaging apparatus 1, a medical image management apparatus 2 (dynamic image processing apparatus), and medical image display apparatus 3. The apparatuses are connected to be able to transmit and receive data through a communication network including a communication line such as a LAN (Local Area Network) or WAN (Wide Area Network). The apparatuses included in the medical information management system 100 conform to a DICOM (Digital Image and Communications in Medicine) standard, and the communication between the apparatuses is performed according to the DICOM standard.

The medical imaging apparatus 1 is a modality such as a CT (Computer Tomography) apparatus, CR (Computed Radiography) apparatus, MRI (Magnetic Resonance Imaging) apparatus, etc. Among the above, the CT apparatus and the CR apparatus irradiate radiation on the patient (subject) and generate image data of a radiation image as a medical image based on a detected result of the radiation. The medical image imaging apparatus 1 writes supplementary information in a header of an image file of a medical image according to the DICOM standard, adds the supplementary information to the radiation image, and generates a DICOM image file. The medical image imaging apparatus 1 operates according to an operation by an operator on a console which is not shown. A plurality of one type of the various modalities may be prepared or one of each of the plurality of types of modalities can be prepared. The number of modalities and the combination are suitably determined according to the necessities of the facility.

The medical image management apparatus 2 is a computer apparatus which accumulates, stores, and manages image data of the medical image generated by the medical image imaging apparatus 1 and supplementary information regarding the medical image. The medical image management apparatus 2 is, for example, a PACS (Picture Archiving and Communication System).

The medical image managed by the medical image management apparatus 2 includes for example, a tomographic image generated by a CT apparatus or MRI apparatus, and a simple X-ray image generated by a CR apparatus. According to the present embodiment, the medical image includes the medical dynamic image obtained when dynamic imaging is performed by the medical image imaging apparatus 1.

Here, "dynamic imaging" is successive radiation imaging of a dynamic state of a target site along a time axis. Specifically, pulsed radiation is repeatedly irradiated from a radiation source (not shown) at a predetermined time interval (pulsed irradiation) or radiation is continuously irradiated without pausing at a low radiation dose (continuous irradiating). With this, imaging is performed a plurality of times successively. The frame image is generated in each of the plurality of imaging, and the medical dynamic image including the above plurality of frame images is generated. Each frame image is applied with a frame number in the order of imaging. The plurality of frame images of the medical dynamic image are displayed by switching the frame images according to the number of the frame image, and with this, the moving image showing the dynamic state of the target site can be played.

For example, a group of a string of related medical images such as medical images imaged in one examination performed in a same site for one patient is called a "series". A plurality of frame images included in the medical dynamic image obtained by the dynamic imaging corresponds to one series.

The dynamic imaging according to the present embodiment is performed in a target site which moves periodically, for example, the lung field, diaphragm, heart, and the like. The site which is the target of dynamic imaging is not limited to the above.

The medical image management apparatus 2 according to the present embodiment is able to generate a secondary medical image based on at least one or more of the plurality of frame images included in the medical dynamic image. Here, the secondary medical image includes a copy of one of the plurality of frame images as is, a high definition still image obtained by enhancing the resolution of one frame image to a high resolution, and a high definition dynamic image including two or more high definition frame images obtained by enhancing the resolution of two or more of the plurality of frame images to a high resolution. The operation regarding generating the secondary medical image is described in detail later.

When there is a request to display information regarding the medical image from the medical image display apparatus 3 through the communication network N, the medical image management apparatus 2 reads the information corresponding to the requested information from a medical image DB (database) 221 (see FIG. 2) and transmits the information to the medical image display apparatus 3. The requested information is displayed on the display of the medical image display apparatus 3.

The medical image display apparatus 3 is a computer apparatus such as a PC used by a doctor. The doctor performs the predetermined operation in the medical image display apparatus 3 and with this, is able to view various information regarding the medical image received from the medical image management apparatus 2.

Next, the configuration of the medical image management apparatus 2 and the medical image display apparatus 3 is described.

Figure 2:
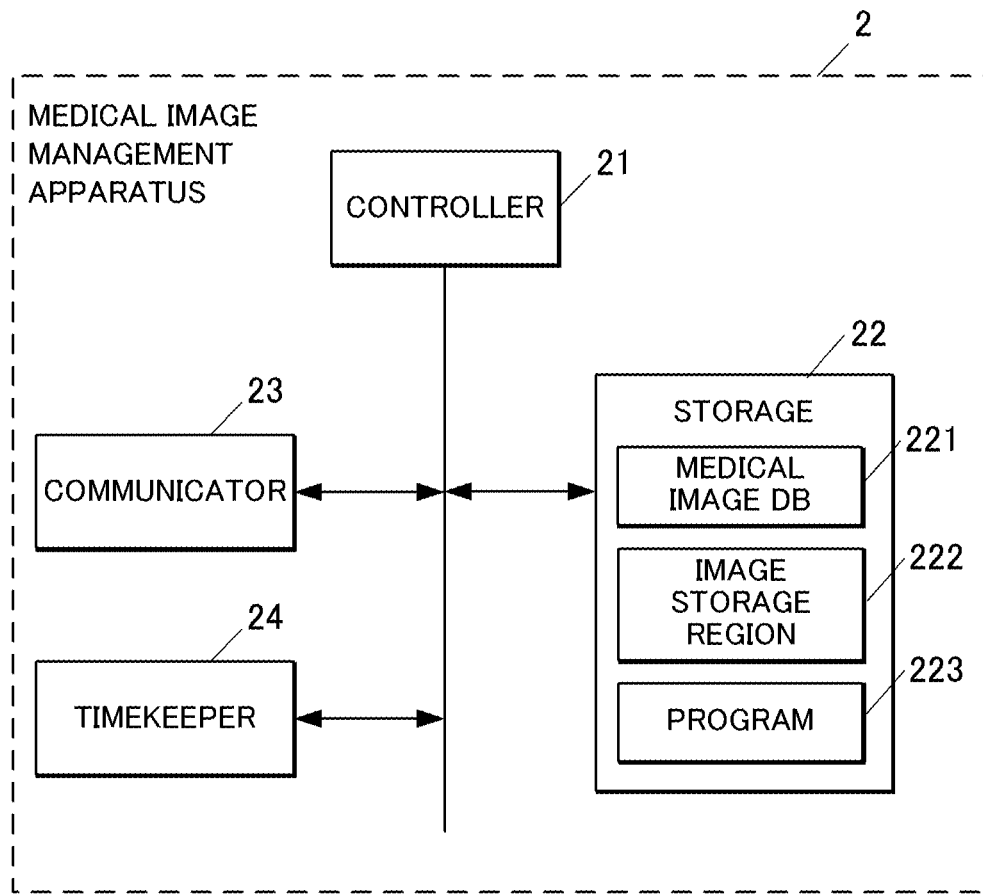
FIG. 2 is a block diagram showing a functional configuration of a medical image management apparatus.

FIG. 2 is a block diagram showing a functional configuration of the medical image management apparatus 2.

As shown in FIG. 2, the medical image management apparatus 2 includes a controller 21 (computer), a storage 22, a communicator 23, a timekeeper 24, and the like, and each unit is connected to each other by a bus.

The controller 21 (hardware processor) includes a CPU (Central Processing Unit), a ROM (Read Only Memory), a RAM (Random Access Memory), and the like, and the controller 21 centrally controls the operation of the processes performed in the units of the medical image management apparatus 2. Specifically, the CPU reads the program 223 stored in the storage 22 and deploys the program 223 in the RAM. The CPU performs various processes according to the program 223. The CPU executes the program 223 and the controller 21 functions as the image generator, recorder, display controller, receiver, and image deleter.

The controller 21 as the image generator executes the process which generates the secondary medical image based on at least one or more of the plurality of frame images included in the medical dynamic image.

The controller 21 as the recorder executes the recording process in which a record is kept showing that the secondary medical image is generated secondarily from an existing medical dynamic image.

The controller 21 as the display controller executes a process to display the generated secondary medical image on the display 34 of the medical image display apparatus 3.

The controller 21 as the receiver receives from the user an instruction specifying one frame image used to generate the secondary medical image.

The controller 21 as the image deleter executes the process to delete the image data of the secondary medical image from the storage 22 when a predetermined storage term passes.

The storage 22 includes a HDD (Hard Disk Drive), a nonvolatile semiconductor memory and stores various data. For example, the storage 22 includes the medical image DB 221 and an image storage region 222. The program 223 is stored in the storage 22. The program 223 may be stored in the ROM of the controller 21.

The medical image DB 221 stores in a searchable manner the supplementary information (information recorded in the header) of the file of the medical image stored in the image storage region 222 and information such as examination conditions regarding the examination (for example, information of the irradiated dose of radiation). In detail, the medical image DB 221 includes a patient information table, an examination information table, a series information table and an image information table.

Patient identification information (for example, patient ID) to identify the patient, various information regarding the patient of the medical image such as name, sex, and birthday of the patient, and the like are stored in the patient information table.

Examination identification information (for example, identification ID) to identify the examination, various information regarding the examination such as the examination date, the doctor in charge, and the like are stored in the examination information table.

Various information regarding the series such as a series number to identify the series in the same examination, type of modality (medical image imaging apparatus 1) which generates the medical image included in the series, examination site, total number of frames when the medical image is the medical dynamic image, frame number applied to the images in the series and the like are stored in the series information table. As described above, the frame number is the number showing imaging order 1 to n (n is total number of frames) of the frame images of the medical dynamic image generated as the same series.

Information regarding various information regarding the image such as image generating time, file pass name showing a storage location of the medical image, examination comment, measured position of lesion, measured result, and the like are stored in the image information table.

The image data, etc. of the medical image is stored in the image storage region 222.

Figure 3:
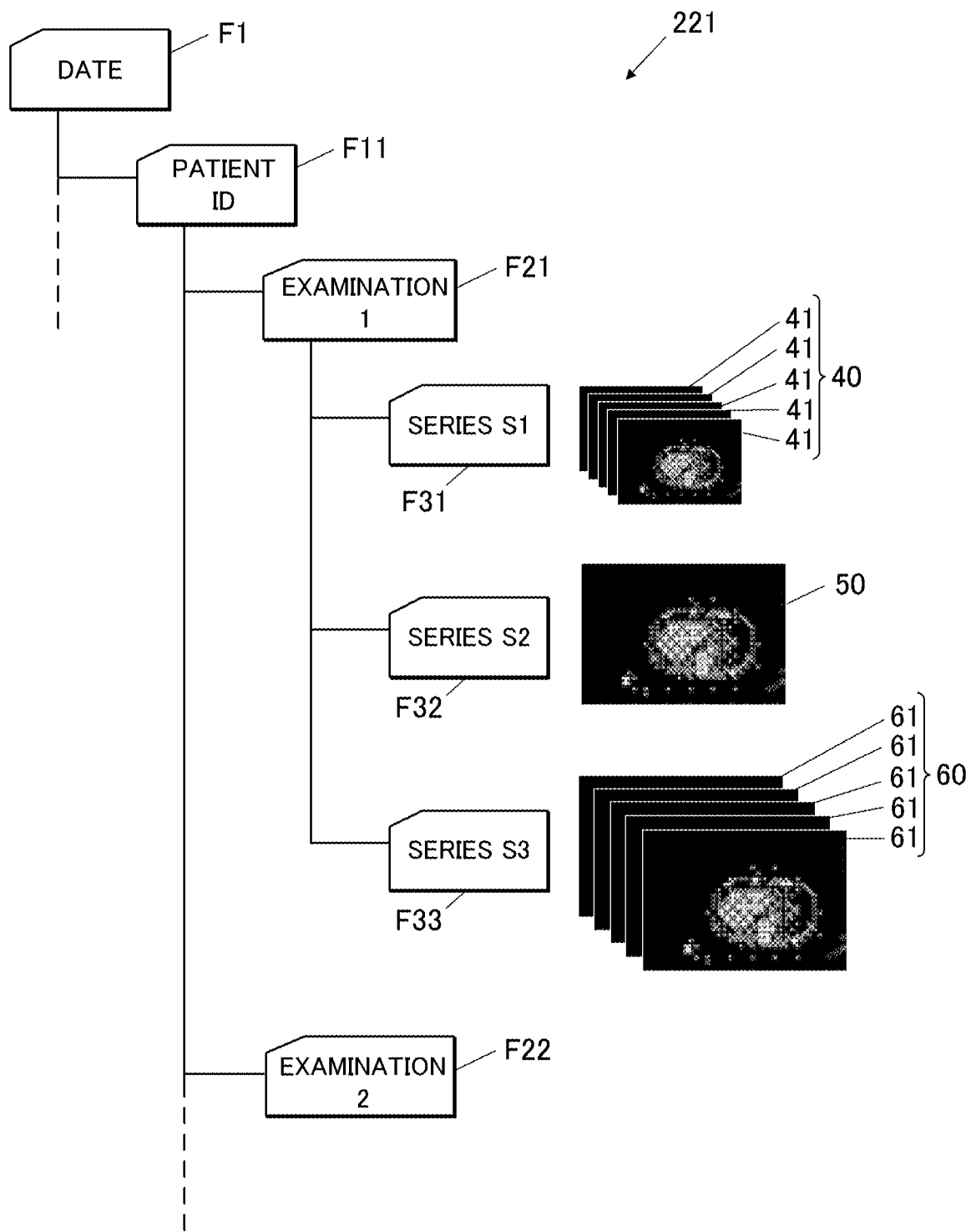
FIG. 3 is a diagram showing a folder configuration in an image storage region.

FIG. 3 is a diagram showing a folder configuration in the image storage region 222. In the image storage region 222, a hierarchy structure is formed in the following order, a date folder generated for each date of the examination (F1), a patient folder generated for each patient (F11), an examination folder generated for each examination (F21, F22), and a series folder generated for each series (F31 to F33). The image data of the medical image is stored grouped according to series in the above series folder.

According to the example shown in FIG. 3, the series folders F31 to F33 are generated in a lower layer of one examination folder F21.

Image data of a medical dynamic image 40 including a plurality of frame images 41 is stored in the series folder F31.

A high definition still image 50 obtained by enhancing to the high resolution the resolution of one frame image 41 of the medical dynamic image 40 is stored in the series folder F32.

A high definition dynamic image 60 including a plurality of high definition frame images 61 obtained by enhancing to the high resolution the resolution of a plurality of frame images 41 of the medical dynamic image 40 is stored in the series folder F33.

Returning to FIG. 2, the communicator 23 includes a network interface, and the data is transmitted and received with external apparatuses connected through the communication network N. For example, the communicator 23 receives image data of the medical image obtained by imaging the patient from the medical image imaging apparatus 1.

The timekeeper 24 includes a timekeeping circuit (RTC: Real Time Clock). The timekeeper 24 keeps the present date and time using the timekeeping circuit and outputs the present date and time to the controller 21.

Figure 4:
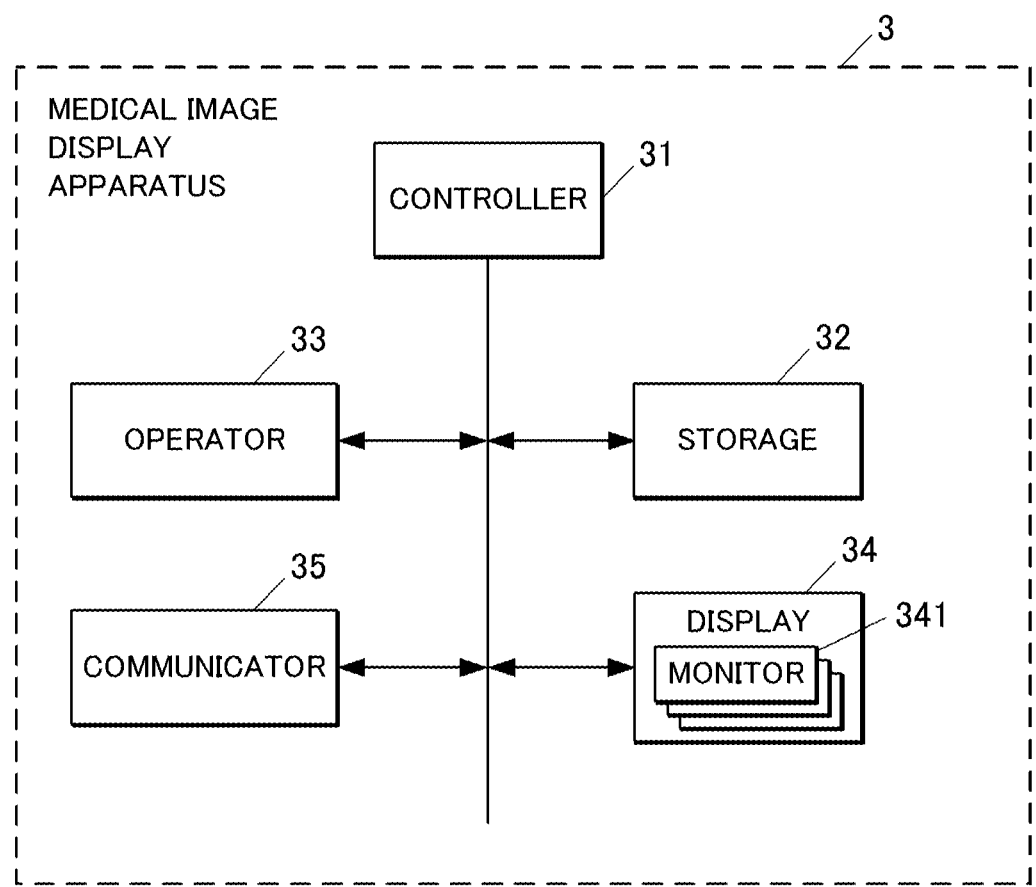
FIG. 4 is a block diagram showing a functional configuration of a medical image display apparatus.

FIG. 4 is a block diagram showing a functional configuration of the medical image display apparatus 3.

The medical image display apparatus 3 includes a controller 31, a storage 32, an operator 33, a display 34, a communicator 35, and the like, and each unit is connected to each other through a bus.

The controller 31 includes a CPU, a ROM, a RAM, etc. and the operation of the processes of each unit of the medical image display apparatus 3 is centrally controlled. Specifically, the CPU reads the various processing programs stored in the ROM, deploys the programs in the RAM and performs various processes according to the program.

The storage 32 includes an HDD, a nonvolatile semiconductor memory, etc. and stores various data and programs.

The operator 33 includes a keyboard including a cursor key, a letter/number input key, and various function keys, and a pointing device such as a mouse. The operator 33 outputs the instruction signal input by the key operation on the keyboard and the mouse operation to the controller 31. The operator 33 may include a touch panel provided overlapped on a monitor 341 of the display 34.

The display 34 includes a monitor 341 such as a LCD (Liquid Crystal Display), and according to the instruction of the display signal input from the controller 31, various screens are displayed. A plurality of monitors 341 can be provided. One or more among the plurality of monitors 341 may have a higher display resolution than the other monitors 341, and the monitor 341 in which the medical image is displayed can be switched depending on the resolution of the medical image as the display target.

The communicator 35 includes a network interface and transmits and receives data with external apparatuses connected through the communication network N.

Next, the operation of the apparatuses in the medical information management system 100 is described centering on the display operation of the medical image in the medical image display apparatus 3 and the generating operation of the secondary medical image in the medical image management apparatus 2.

In the medical information management system 100, in response to the operation of the medical image display apparatus 3 by the user such as the doctor, the data of the specified medical image is transmitted from the medical image management apparatus 2 to the medical image display apparatus 3, and the information display screen 70 including the medical image is displayed on the display 34 of the medical image display apparatus 3.

Figure 5:
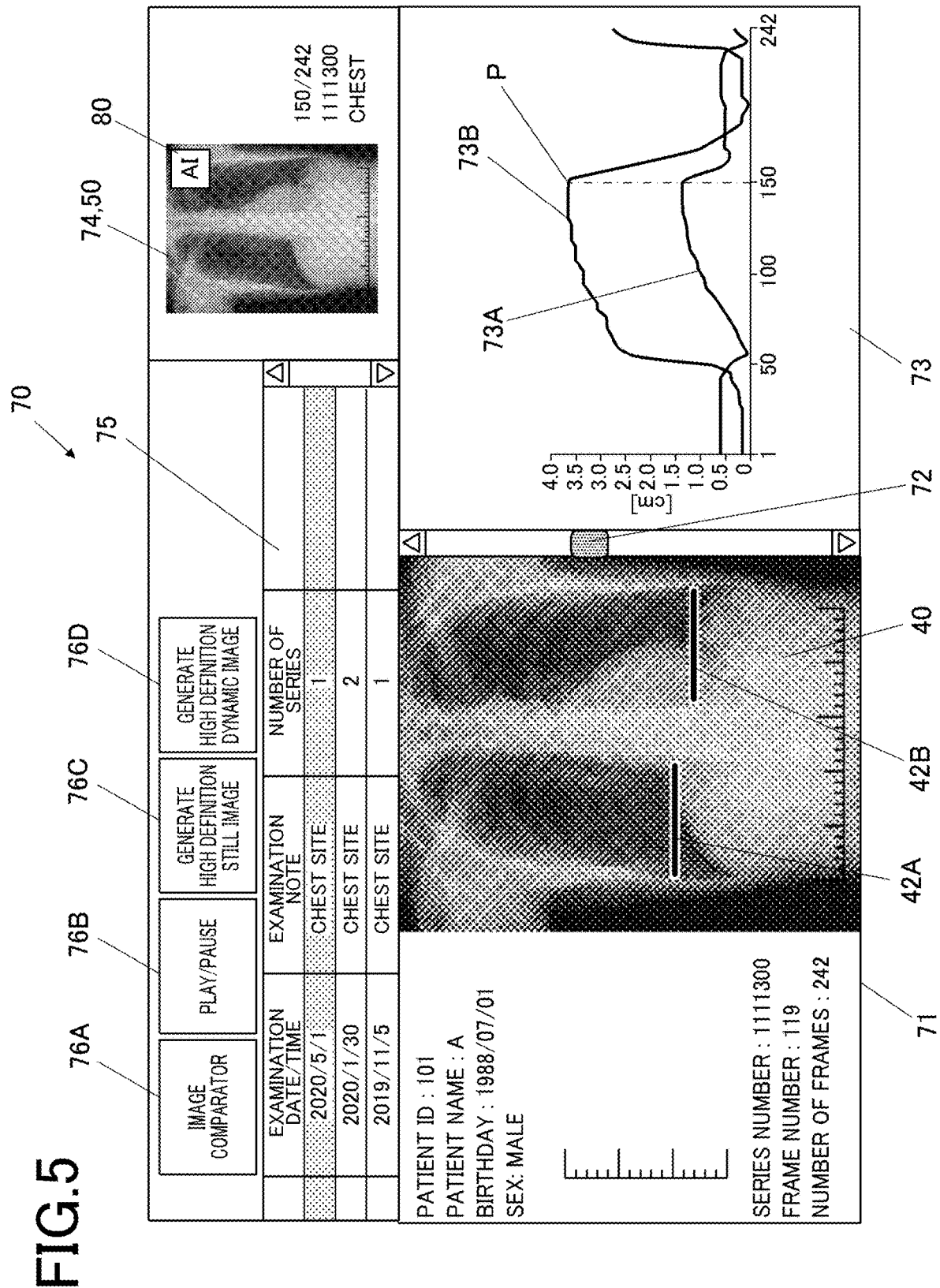
FIG. 5 is a diagram showing an example of an information display screen.

FIG. 5 is a diagram showing an example of the information display screen 70.

FIG. 5 illustrates an example of an information display screen 70 when a request for a display of the medical dynamic image 40 of the lung field is made.

In the information display screen 70, the medical dynamic image 40, image information 71, a scroll bar 72, a dynamic graph 73, a thumbnail image 74, an examination list 75, and operation buttons 76a to 76d are displayed.

Here, the medical dynamic image 40 is displayed on the bottom left side of the information display screen 70. Regarding the medical dynamic image 40, the playing of the moving image may start when the information display screen 70 is displayed or the playing of the moving image may start in response to a predetermined operation (for example, operation to select the operation button 76b). Indicators 42a and 42b showing a predetermined position in the lung field (for example, position of diaphragm) are displayed overlapped on the medical dynamic image 40.

The image information 71 includes information regarding the patient and information regarding the medical dynamic image 40 being played. The information regarding the patient includes, the patient ID, the patient name, the birthday of the patient, the sex of the patient, and the like. Information regarding the medical dynamic image 40 includes the series number, the frame number of the frame image being displayed and the total number of frames. The items of the image information 71 shown in FIG. 5 are merely examples, and other than the above, the inspection date/time and the image generating date/time can be included. The image information 71 can be displayed overlapped with the medical dynamic image 40.

The scroll bar 72 is provided extending along the up and down direction on the right side of the medical dynamic image 40. A cursor which moves in the up and down direction is provided in the scroll bar 72. The cursor is positioned at the upper end of the scroll bar 72 at the point of the start of the medical dynamic image 40. The cursor moves downwards as the playing time of the moving image passes, and at the point of the end of the medical dynamic image 40, the cursor is positioned at the lower end. By performing the operation to move the cursor up and down, the predetermined frame image in the medical dynamic image 40 can be selected. When the selection of the frame image is made by the cursor, the playing of the medical dynamic image 40 is paused at the position of the above frame image. The operation is not limited to the above, and the medical dynamic image 40 can be automatically played from the position of the selected frame image. The method of selecting the frame image is not limited to the method using the cursor of the scroll bar 72, and the method to input the frame number in the text box (not shown) or the method to select one frame number from the frame numbers displayed as a drop down list (not shown) may be employed.

The dynamic graph 73 shows the position of the indicators 42a and 42b in the up and down direction in the image with relation to the frame number of the medical dynamic image 40. The line 73a corresponds to the indicator 42a and the line 73b corresponds to the indicator 42b. It is possible to visibly confirm the cycle of the movement in the lung field and the degree of the movement using the dynamic graph 73.

The thumbnail image 74 is a still image showing one frame image in the displayed medical dynamic image 40 in a reduced state. Here, the frame image with the frame number "150" specified by a method described below is displayed, but the frame image to be displayed is not limited to the above, and the first frame image may be displayed.

The image data of the thumbnail image 74 is normally generated and managed separately from the image data of the medical dynamic image 40. The image data of the thumbnail image 74 may be image data of one frame image that is copied or may be a later described high definition still image. The thumbnail image 74 managed separately from the medical dynamic image 40 is one form of the secondary medical image.

In the example shown in FIG. 5, the high definition still image 50 is used as the thumbnail image 74. An annotation mark 80 showing that it is a secondary medical image is displayed overlapped with the thumbnail image 74. For example, the image of the annotation mark 80 is embedded in the image data of the high definition still image 50 as the thumbnail image 74. The controller 21 (display controller) of the medical image management apparatus 2 transmits the image data to the medical image display apparatus 3, and displays the annotation mark 80 together with the thumbnail image 74.

The examination list 75 displays in a list the information of all of the examinations performed on the patient who is the target of examination of the medical dynamic image 40. The examination list 75 clearly shows by highlighting the examination where the medical dynamic image 40 being displayed belongs. Here, for each examination, the items such as the examination date/time, examination remarks, and the number of series are displayed. However, the displayed items are not limited to the above.

The operation button 76a is a button to perform the process to display two medical images aligned for comparison.

The operation button 76b is a button to perform the process of switching between playing and pausing the medical dynamic image 40.

The operation button 76c is a button to perform the process of enhancing the resolution of the frame image selected by the above described method of selection to a high resolution and generating the high definition still image 50.

The operation button 76d is a button to perform the process of enhancing the resolution of the frame images of the medical dynamic image 40 to a high resolution and generating the high definition dynamic image 60.

The high definition still image 50 and the high definition dynamic image 60 are one form of the secondary medical image generated from the medical dynamic image 40.

The process of enhancing the resolution of the frame image to a high resolution in order to generate the high definition still image 50 and the high definition dynamic image 60 is performed by the controller 21 (image generator) of the medical image management apparatus 2. The process of enhancing the resolution to a high resolution is performed by the following method, for example, a learning model generated by machine learning is used to estimate a pixel value after the resolution is enhanced and the noise is removed. For example, other image data which shows the same examination site and which is generated by the medical image imaging apparatus 1 the same as the medical image imaging apparatus 1 used for generating the frame image as the target of enhancing the resolution to a high resolution is used as the training data of machine learning.

The high definition dynamic image 60 is not limited to enhancing the resolution of all of the frame images in the medical dynamic image 40 to a high resolution, and the resolution of one or more of the frame images may be enhanced to be high resolution frame images. That is, the high resolution dynamic image 60 may be a dynamic image corresponding to a part of the medical dynamic image 40. In this case, the range of the frame numbers in which the resolution is enhanced to a high resolution may be specified by the user.

The high definition still image 50 is not limited to enhancing the resolution of one frame image to a high resolution, and the high definition still image 50 may be generated based on two or more frame images (two or more of some of the frame images among the plurality of frame images included in the medical dynamic image 40). For example, two or more of the high definition frame image data obtained by enhancing the resolution of each of the two or more frame images to a high resolution may be combined to generate one high definition still image 50. Alternatively, two or more frame images may be combined while also enhancing the resolution to a high resolution and one high definition still image 50 may be generated. In these cases, the frame number of the two or more frame images used to generate the high definition still image 50 can be specified by the user.

Together with the generating of the image data of the high definition still image 50 or the high definition dynamic image 60 as the secondary medical image, the controller 21 (recorder) performs the recording process in which the record is kept to show that the generated secondary medical image is generated as a secondary image from an existing medical dynamic image 40.

Here, the recording process is a process in which an annotation mark 80 (see FIG. 6 and FIG. 7) (note mark) is displayed with the high definition still image 50 or the high definition dynamic image 60. The recording process includes the following first manner and the second manner.

The recording process in the first manner is a process in which the image data of the high definition still image 50 or the high definition dynamic image 60 is updated to the image data of the image including the annotation mark 80. When the display process is performed using the updated image data, the high definition still image 50 or the high definition dynamic image 60 including the annotation mark 80 is displayed.

The recording process in the second manner is a process in which the annotation information indicating that the images are secondary medical images is added as the supplementary information in the header (supplementary data) of the image data of the high definition still image 50 or the high definition dynamic image 60. By performing the recording process, the annotation information is referred when the high definition still image 50 or the high definition dynamic image 60 is displayed, and when the annotation information is recorded, the annotation mark 80 is displayed together with the secondary medical image.

Figure 6:
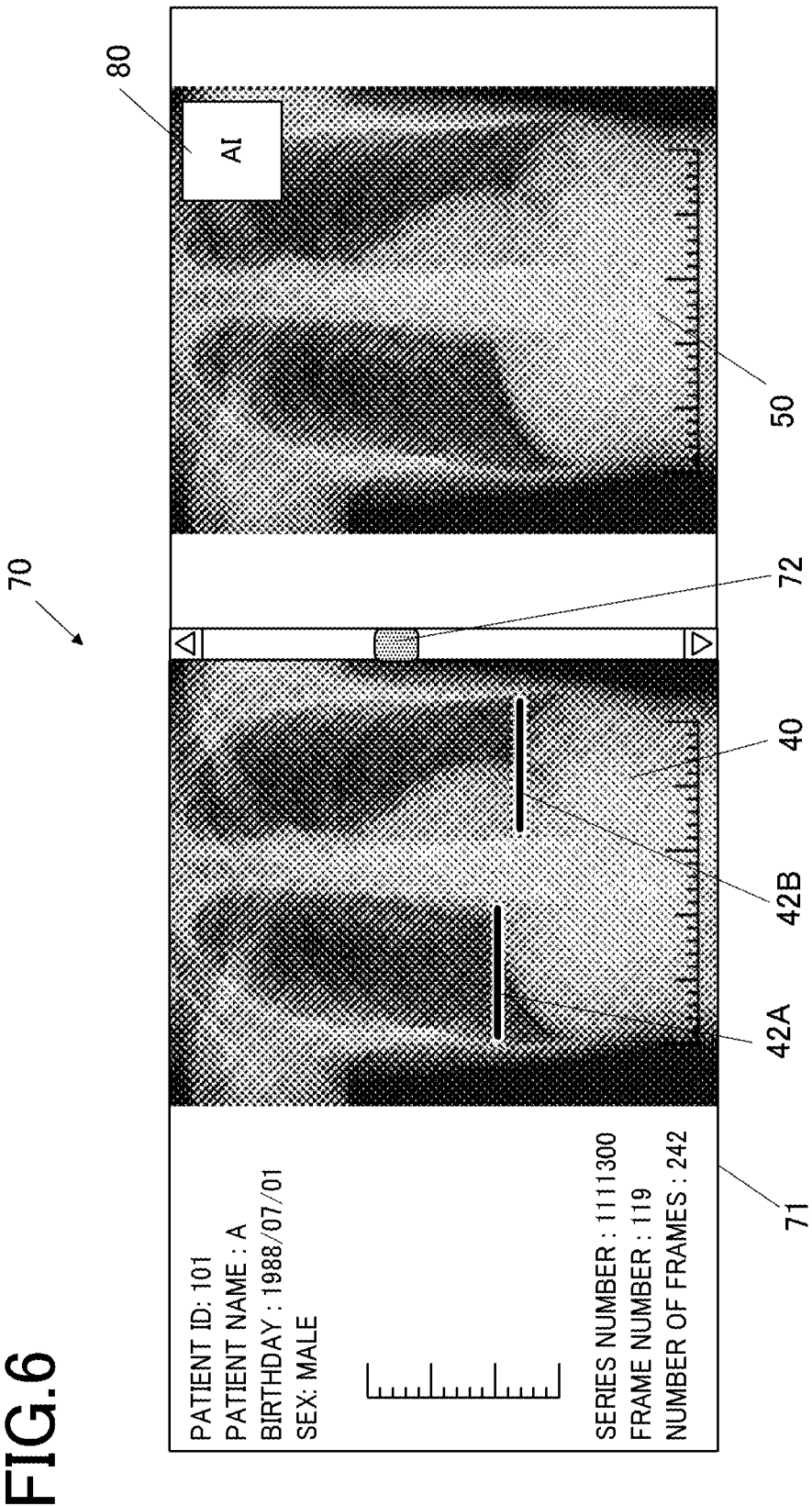
FIG. 6 is a diagram showing an example of an information display screen when a medical dynamic image and a high definition still image are displayed aligned.

FIG. 6. is a diagram showing an example of an information display screen 70 when the medical dynamic image 40 and the high definition still image 50 are displayed aligned.

For example, after the high definition still image 50 is generated in response to the operation of selecting the operation button 76c, when the operation button 76a is selected and the user inputs an instruction to display the medical dynamic image 40 and the high definition still image 50 in an aligned state, the information display screen 70 shown in FIG. 6 is displayed in the display 34 of the medical image display apparatus.

In the information display screen 70, the high definition still image 50 in which the resolution is enhanced to the high resolution is displayed aligned on the right side of the medical dynamic image 40. Therefore, together with the medical dynamic image 40 with the low resolution, the user is able to confirm the high definition still image 50 with the high resolution corresponding to one frame of the medical dynamic image 40.

On the upper right of the high definition still image 50, the annotation mark 80 showing that the image is a secondary medical image is displayed. With this, the user is able to understand that the high definition still image 50 cannot be used in interpretation for the purpose of diagnosis.

Figure 7:
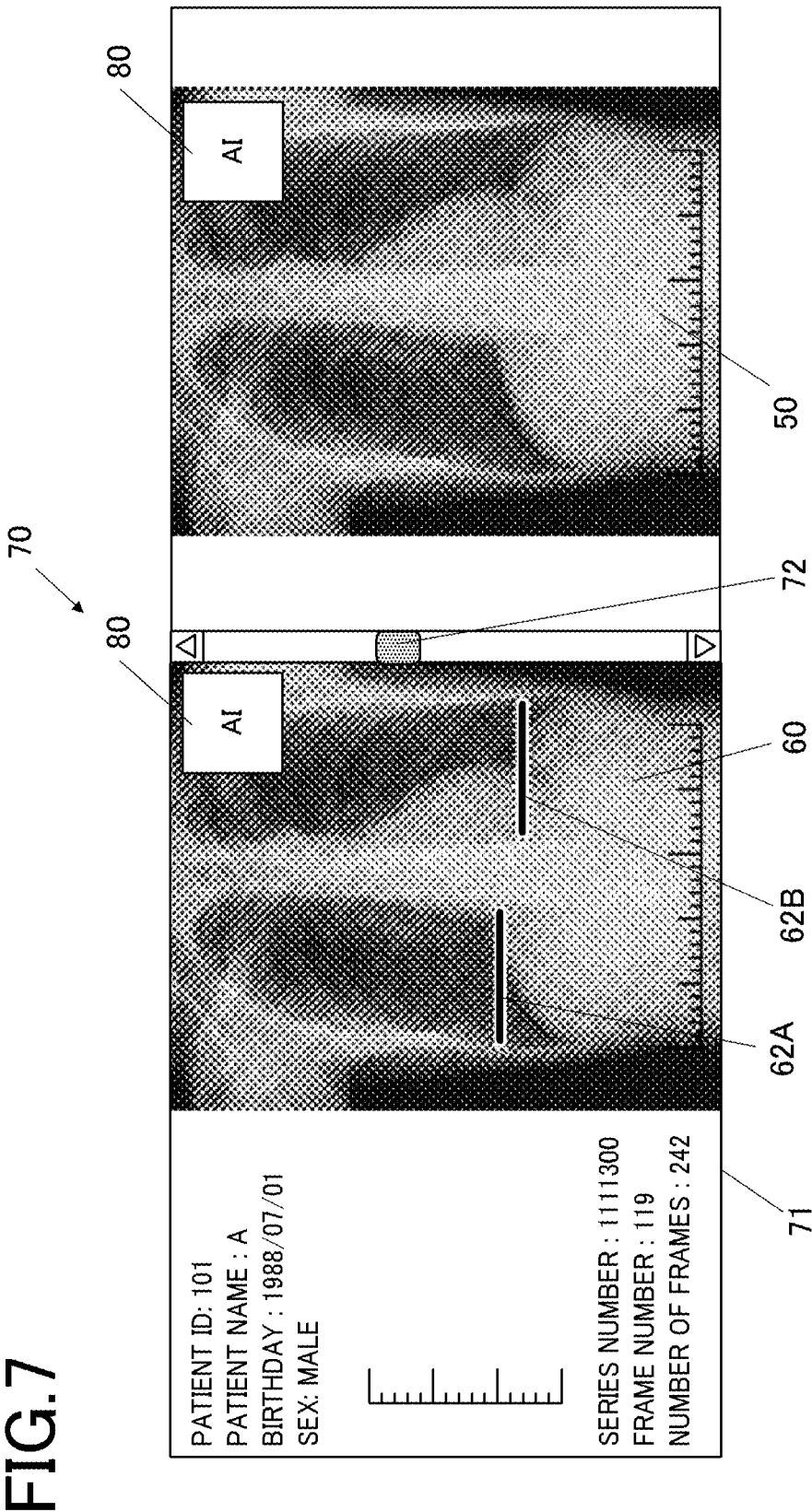
FIG. 7 is a diagram showing an example of an information display screen when a high definition dynamic image and a high definition still image are displayed aligned.

FIG. 7 is a diagram showing an example of an information display screen 70 when the high definition dynamic image 60 and the high definition still image 50 are displayed aligned.

After the high definition still image 50 is generated in response to the operation of selecting the operation button 76c and the high definition moving image 60 is generated in response to the operation of selecting the operation button 76d, when the operation button 76a is selected and the user inputs the instruction to display the high definition dynamic image 60 and the high definition still image 50 aligned, the information display screen 70 shown in FIG. 7 is displayed on the display 34 of the medical image display apparatus 3.

This information display screen 70 corresponds to the information display screen 70 shown in FIG. 6 with the medical dynamic image 40 switched to the high definition dynamic image 60. The indicators 62a and 62b showing the predetermined position in the lung field (for example, position of diaphragm) are displayed overlapped with the high definition dynamic image 60. According to such information display screen 70, the user is able to confirm together with the high definition still image 50 with the high resolution the high definition dynamic image 60 with a resolution higher than the originally generated medical dynamic image 40.

The annotation mark 80 showing that the image is the secondary medical image is displayed in the upper right of each of the high definition still image 50 and the high definition dynamic image 60. With this, the user is able to understand that the high definition still image 50 and the high definition dynamic image 60 cannot be used to be interpreted for the purpose of diagnosis.

In FIG. 6 and FIG. 7, the letters "AI" are used as the annotation mark 80 to show that the resolution is enhanced to a high resolution by AI (Artificial Intelligence). The annotation mark 80 is not limited to the above, and any letter or shape determined in advance can be used as the mark to show that the image is a secondary medical image. The same can be said for the annotation mark 80 added to the thumbnail image 74 shown in FIG. 5.

The high definition still image 50 shown in FIG. 6 and FIG. 7 is generated by enhancing the resolution of the frame image selected by the user but the controller 21 can automatically determine the frame image used in the high definition still image 50. For example, the controller 21 (image generator) may enhance the resolution of one frame image corresponding to a specific timing determined by a cyclic operation of the subject and generate the high definition still image 50. For example, the frame image (here, the frame image with the frame number "150") corresponding to the point P in which the position of the indicator 42b is to be maximum in the dynamic state graph 73 shown in FIG. 6 is specified, and the resolution of the frame image can be enhanced to generate the high definition still image 50. The point P corresponds to the timing (the timing that the lung field contracts the most by expiration) that the diaphragm is in the upper limit position in the cycle corresponding to one breath. Instead of the above, the frame image at the timing (the timing that the lung field expands most by inspiration) that the diaphragm is in the lower limit position in the cycle corresponding to one breath can be specified as the target image in which the resolution is enhanced to the high resolution.

As described above, since the controller 21 generates the high definition still image 50 automatically, the high definition still image 50 can be generated in the state without the instruction from the user to generate the high definition still image 50. The high definition still image 50 in this case can be used as the thumbnail image 74 shown in FIG. 4, for example.

Next, the control procedure of the information display process to display the information display screen on the medical image display apparatus 3 is described. Below, the first to third information display processes in which the method to specify the frame image in which the resolution is enhanced to the high resolution and/or the process to display the annotation mark 80 is different from each other are described.

(First Information Display Process)

Figure 8:
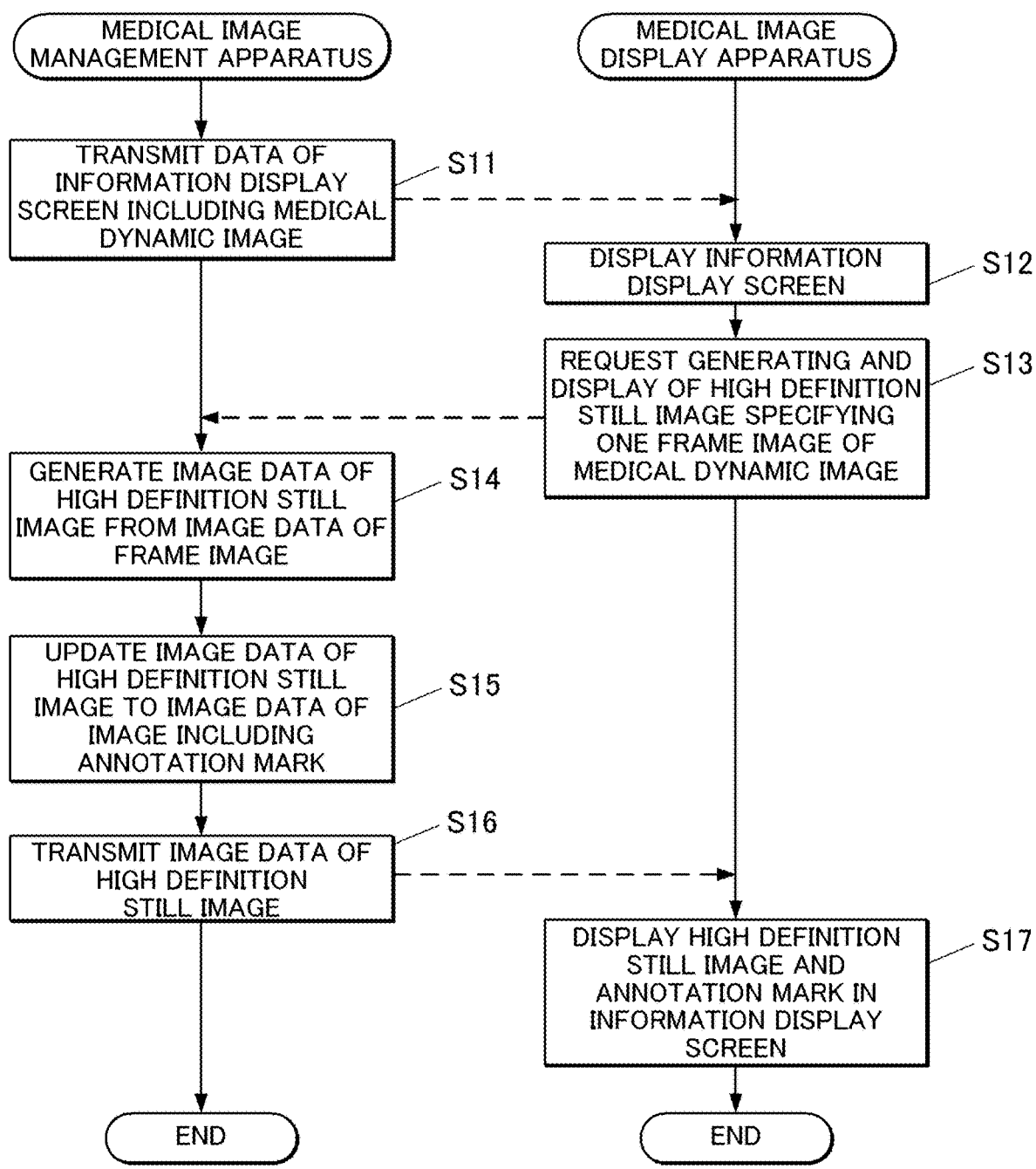
FIG. 8 is a flowchart showing a control procedure of a first information display process.

FIG. 8 is a flowchart showing a control procedure of the first information display process.

FIG. 8 shows in parallel as a ladder chart the process executed by the controller 21 of the medical image management apparatus 2 and the process executed by the controller 31 of the medical image display apparatus 3. Hereinbelow, the controller 21 (31) controlling the communicator 23 (35) to transmit data is simply described as "the controller 21 (31) transmits data".

The first information display process starts when the display request of the information display screen 70 including the medical dynamic image 40 is transmitted from the medical image display apparatus 3 to the medical image management apparatus 2 in response to the operation of the user in the medical image display apparatus 3.

When the first information display process starts, the controller 21 of the medical image management apparatus 2 generates the data of the information display screen 70 including the image data of the specified medical dynamic image 40 and transmits the data to the medical image display apparatus 3 (step S11).

The controller 31 of the medical image display apparatus 3 displays on the display 34 the information display screen 70 (FIG. 4) based on the received data (step S12).

When the user inputs the instruction to generate and display the high definition still image 50 corresponding to one of the frame images of the medical dynamic image 40, the controller 31 transmits a request to generate and display the high definition still image 50 of the specified frame image to the medical image management apparatus 2 (step S13).

The controller 21 (receiver) of the medical image management apparatus 2 which receives the request receives the instruction from the user specifying one frame image. The controller 21 (image generator) enhances the resolution of the specified frame image to the high resolution and generates the image data of the high definition still image 50 (step S14).

The controller 21 (recorder) executes the recording process to keep a record showing that the high definition still image 50 is generated as a secondary image from the existing medical dynamic image 40. That is, in the recording process, the controller 21 updates the image data of the high definition still image 50 to the image data of the image including the high definition still image 50 and the annotation mark 80 (step S15).

The controller 21 (display controller) transmits the image data of the high definition still image 50 in which the recording process is performed in step S15 to the medical image display apparatus 3 (step S16). With this, the controller 21 (display controller) displays the high definition still image 50 with the annotation mark 80 based on the image data on the display 34 of the medical image display apparatus 3, and the controller 21 displays the high definition still image 50 with the medical dynamic image 40 in the information display screen 70 on the display 34.

The controller 31 of the medical image display apparatus 3 performs the process to display the high definition still image 50 including the annotation mark 80 in the information display screen 70 based on the received image data of the high definition still image 50 (step S17).

When step S16 and step S17 end, the controller 21 and the controller 31 ends the first information display process.

When the instruction to generate and display the high definition dynamic image 60 is received from the user, the resolution of the plurality of frame images is enhanced and the image data of the high definition dynamic image 60 is generated in step S14, the annotation mark 80 is added to the image data in step S15, and the image data of the high definition dynamic image 60 is transmitted to the medical image display apparatus 3 in step S16.

(Second Information Display Process)

Figure 9:
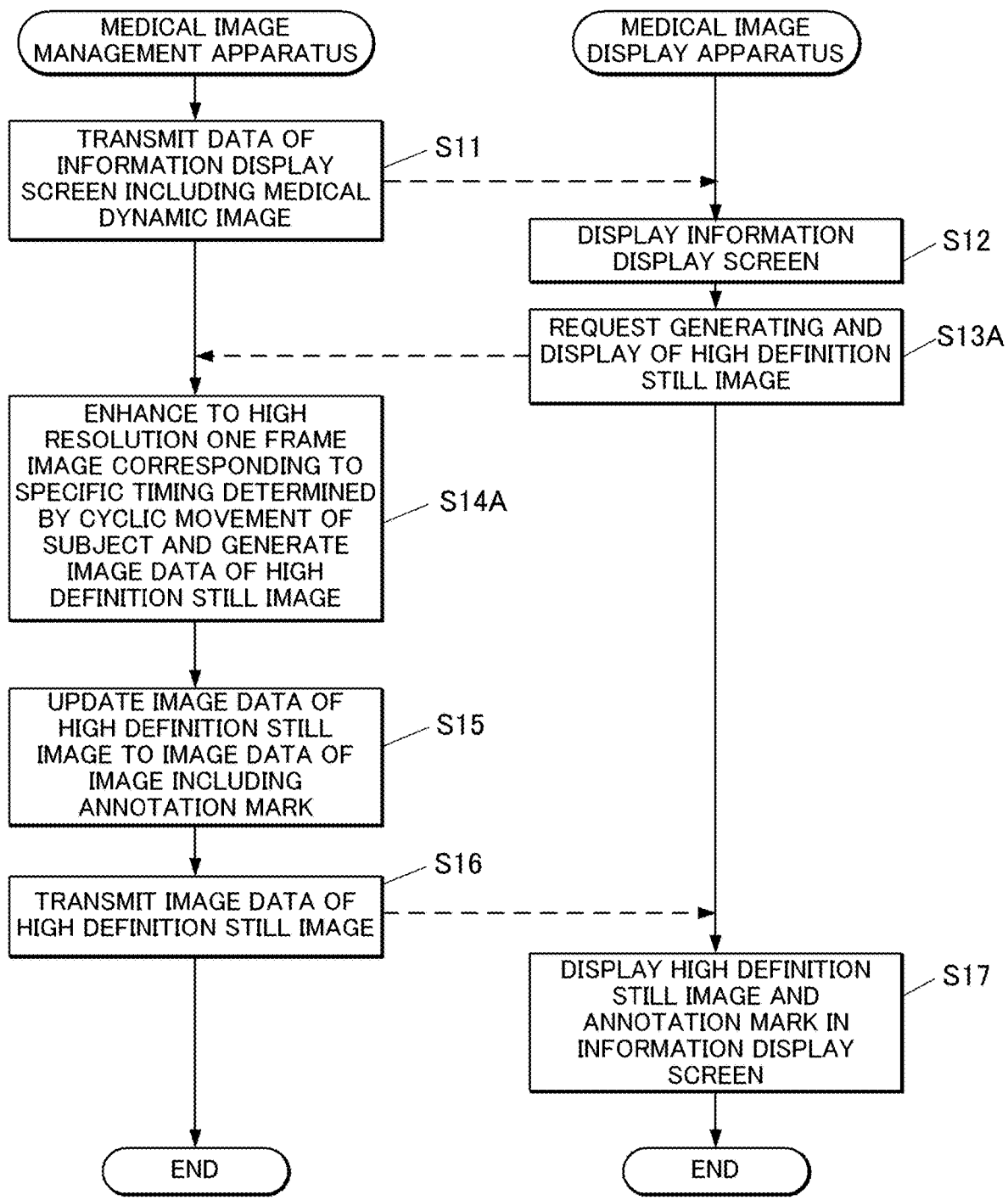
FIG. 9 is a flowchart showing a control procedure of a second information display process.

FIG. 9 is a flowchart showing the control procedure of the second information process.

The flowchart shown in FIG. 9 corresponds to the flowchart shown in FIG. 8 with the steps S13 and S14 switched to steps S13a and S14a, respectively. The second information display process is different from the first information display process in that the controller 21 automatically specifies the frame image to generate the high definition still image 50. The differences from the flowchart shown in FIG. 8 is described below.

When step S12 ends, in response to the input from the user instructing the generating and the displaying of the high definition still image 50, the controller 31 of the medical image display apparatus 3 transmits the request to generate and display the high definition still image 50 to the medical image management apparatus 2 (step S13a). Here, the frame image with which the high definition still image 50 is generated is not specified.

The controller 21 (image generator) of the medical image management apparatus 2 which receives the request enhances to a high resolution the resolution of one frame image corresponding to a specific timing determined by the cyclic operation of the subject and generates the image data of the high definition still image 50 (step S14a). For example, the frame image corresponding to the point P in the dynamic graph 73 shown in FIG. 6 is specified, the resolution of the frame image is enhanced to a high resolution, and the image data of the high definition still image 50 is generated.

The process thereafter is the same as FIG. 8.

According to such second information display process, the suitable high definition still image 50 which represents the medical dynamic image 40 can be generated without receiving the instruction from the user specifying the frame image.

(Third Information Display Process)

Figure 10:
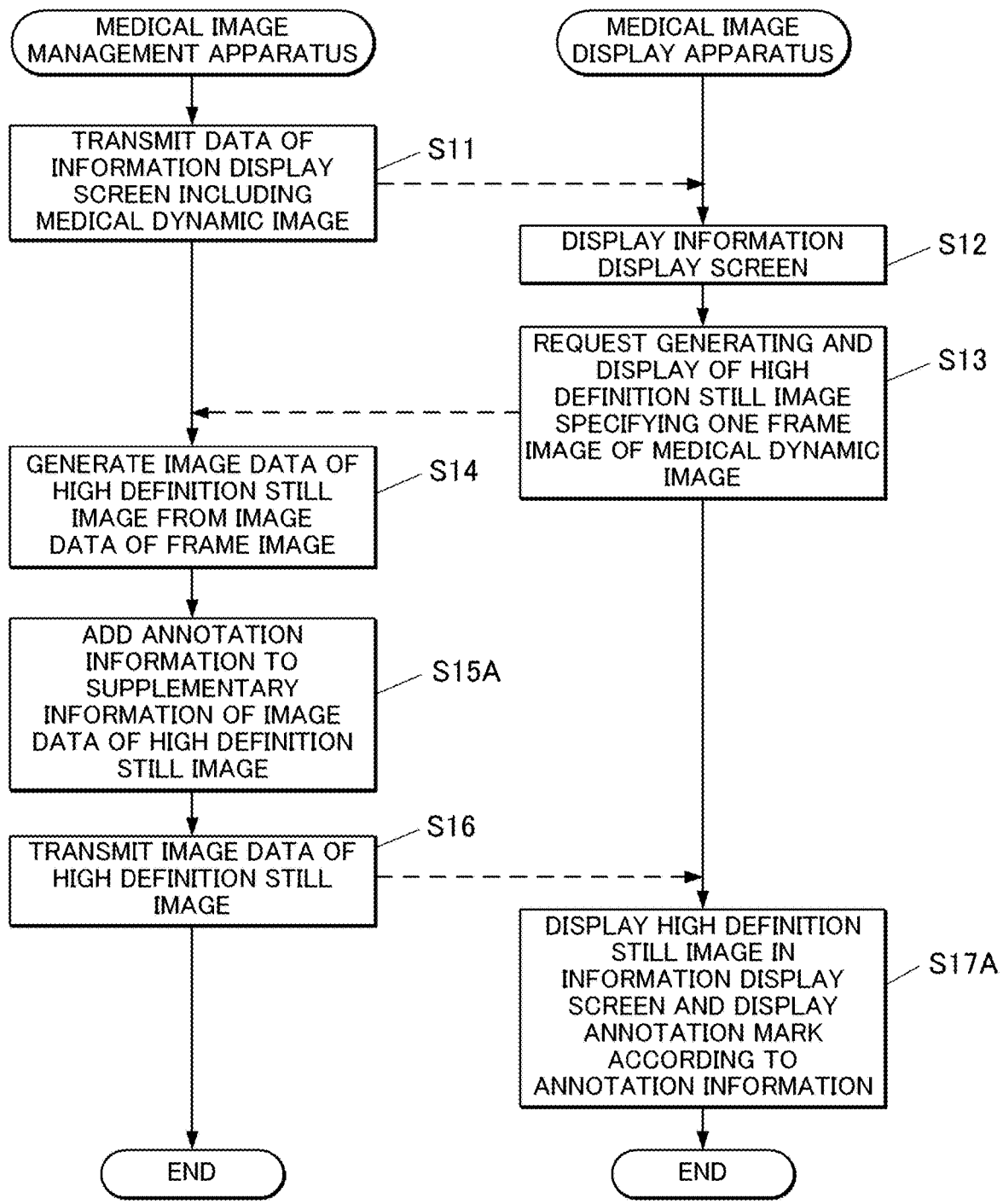
FIG. 10 is a flowchart showing a control procedure of a third information display process.

FIG. 10 is a flowchart showing the control procedure of the third information display process.

The flowchart shown in FIG. 10 corresponds to the flowchart shown in FIG. 8 with the steps S15 and S17 changed to steps S15a and S17a, respectively. The third information display process is different from the first information display apparatus in that the recording process to display the annotation mark 80 is different. Hereinbelow, the points different from the flowchart shown in FIG. 8 are described.

When the image data of the high definition still image 50 is generated in step S14, as the recording process, the controller 21 (recorder) of the medical image management apparatus 2 records the annotation information showing that the image is the secondary medical image in the header of the image data of the high definition still image 50 (step S15a).

The controller 21 (display controller) transmits the image data of the high definition still image 50 including the header recording the annotation information (step S16). With this, the controller 21 (display controller) displays the high definition still image 50 with the annotation mark 80 on the display 34 based on the annotation information of the header.

Based on the image data of the received high definition still image 50, the controller 31 of the medical image display apparatus 3 performs the process to display the high definition still image 50 in the information display screen 70 and performs the display to overlap the annotation mark 80 in response to the annotation information of the header overlapped on the high definition still image 50 (step S17a).

According to such third information display process, the annotation mark 80 can be displayed without directly attaching the annotation mark 80 to the image data of the high definition still image 50.

The second information display process and the third information display process can be combined. That is, steps S15 and S17 in the flowchart shown in FIG. 9 can be switched to steps S15a and S17a in the flowchart shown in FIG. 10.

Next, the data deleting process executed in the medical image management apparatus 2 is described.

The number of pixels in the high definition frame images included in the high definition still image 50 and the high definition dynamic image 60 is larger than the frame images included in the original medical dynamic image 40, and the amount of data is large. Therefore, in order to prevent lack of capacity in the storage 22, a storage term is set for the image data of the high definition still image 50 and the high definition dynamic image 60, and the data deleting process is executed to sequentially delete the image data in which the storage term elapsed.

Figure 11:
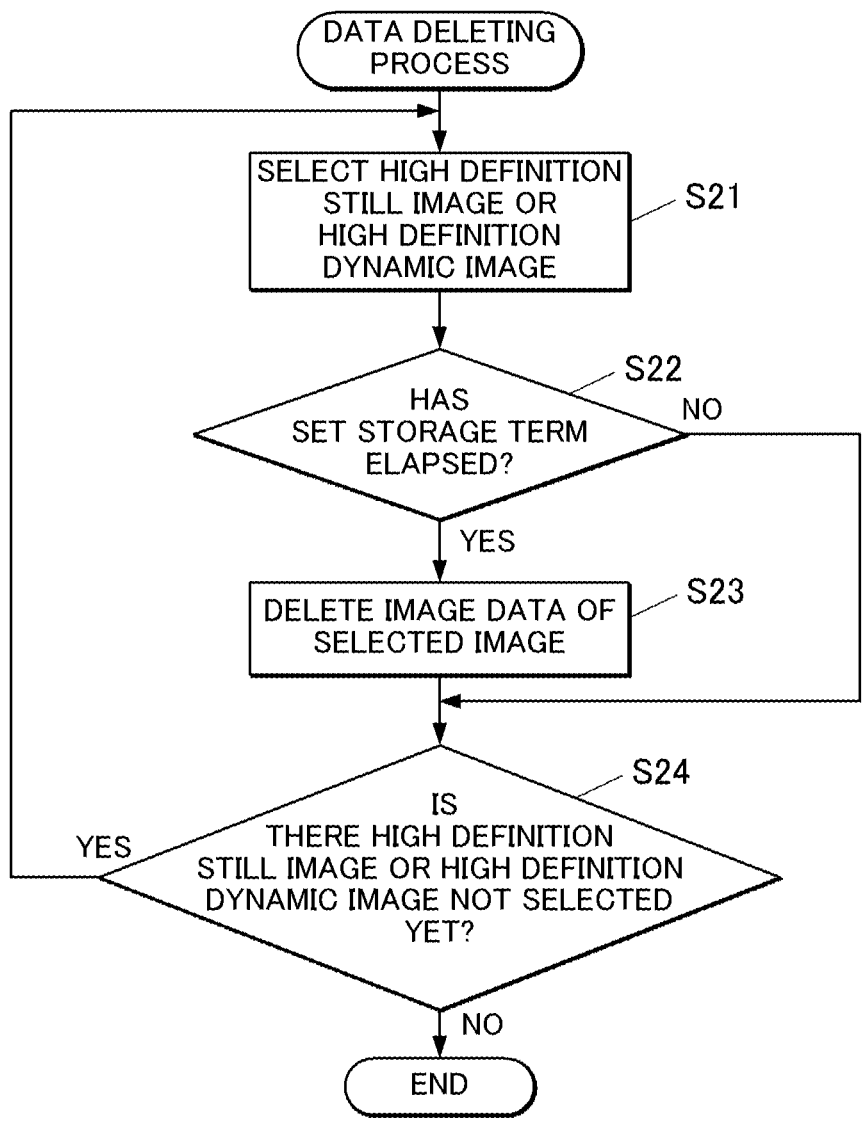
FIG. 11 is a flowchart showing a control procedure of a data deleting process.

FIG. 11 is a flowchart showing the control procedure by the controller 31 in the data deleting process.

The data deleting process is performed periodically, for example, once a week, once a month, or the like. The data deleting process is executed by the controller 21 as the data deleter.

When the data deleting process starts, the controller 21 selects one high definition still image 50 or the high definition dynamic image 60 (step S21), and determines whether the set storage term for the selected high definition still image 50 or the high definition dynamic image 60 elapsed (step S22). Specifically, the controller 21 obtains from the medical image DB 221 the date/time that the selected high definition still image 50 or the high definition dynamic image 60 is received, obtains the present date/time from the timekeeper 24, and compares the term from the received date/time to the present with the storage term to determine whether the storage term elapsed.

When it is determined that the storage term elapsed ("YES" in step S22), the controller 21 deletes the image data of the selected high definition still image 50 or the high definition dynamic image 60 from the storage 22 (step S23).

When step S23 ends, or it is determined that the storage term has not elapsed in step S22 ("NO" in step S22), the controller 21 determines whether there is the high definition still image 50 or the high definition dynamic image 60 which is not selected yet (step S24). When it is determined that there is the high definition still image 50 or the high definition dynamic image 60 which is not selected yet ("YES" in step S24), the controller 21 returns the process to step S21. When it is determined that all of the high definition still images 50 and the high definition dynamic images 60 are selected ("NO" in step S24), the controller 21 ends the data deleting process.

As described above, the medical image management apparatus 2 as the dynamic image processing apparatus according to the present embodiment processes the image data of the medical dynamic image 40 showing a dynamic state of the subject including a plurality of frame images obtained by successively imaging the subject. The medical image management apparatus 2 includes a controller 21. Based on at least one or more of the plurality of frame images included in the medical dynamic image 40, the controller 21 generates the high definition still image 50 and the high definition dynamic image 60 as the secondary medical image (image generator). The controller 21 executes the recording process in which the record is kept to show that the secondary medical image is generated secondarily from the existing medical dynamic image 40 (recorder).

According to the above, it is possible to obtain a (secondary) medical image separate from the medical dynamic image 40 without performing the radiation imaging separately from the radiation imaging for the medical dynamic image 40. Therefore, it is possible to decrease the number of times the radiation imaging is performed and the duration of the radiation imaging in the examination. Consequently, the efficiency of the examination is enhanced and the burden on the patient (received dose, etc.) can be decreased.

However, the secondary medical image is not exactly the image obtained by imaging the patient. Therefore, medical problems such as error in diagnosis may occur if the image is interpreted for diagnosis.

According to the above-described embodiment, the recording process is performed on the secondary medical image and the display of the annotation mark 80 is performed according to the recording process. Therefore, it is possible to suppress the medical problems occurring due to erroneously using and interpreting the secondary medical image.

Each of the plurality of frame images is an image generated according to the irradiation of radiation on the target. By generating and using the secondary medical image form such frame images, it is possible to suppress the radiation dose the patient receives.

The controller 21 displays the secondary medical image on the display 34 (display controller), and based on the result of the recording process, the controller 21 displays the annotation mark 80 showing that the secondary medical image is secondarily generated from the existing medical dynamic image 40 together with the secondary medical image on the display 34 (display controller). With this, the user is able to visually and intuitively understand that the high definition still image 50 cannot be used when interpreting the image in the diagnosis.

In the recording process, the controller 21 updates the image data of the secondary medical image to the image data of the image including the secondary medical image and the annotation mark 80 (recorder). Based on the image data updated by the recorder, the controller 21 displays the secondary medical image and the annotation mark 80 on the display 34 (display controller). With this, it is possible to always display the annotation mark 80 in the image when the secondary medical image is displayed. Consequently, it is possible to more reliably suppress problems such as erroneously using the secondary medical image.

In the recording process, the controller 21 performs the recording of the supplementary data of the image data of the secondary medical image (recorder), and based on the supplementary data in which the recording is performed, the controller 21 displays the secondary medical image together with the annotation mark 80 on the display 34 (display controller). With this, the annotation mark 80 can be displayed without processing the image data itself of the secondary medical image.

When the thumbnail image 74 of the secondary medical image is displayed on the display 34, the controller 21 displays the thumbnail image 74 together with the annotation mark 80 (display controller). With this, it is possible to show that the thumbnail image 74 is the secondary medical image without selecting and enlarging the display of the thumbnail image 74.

The controller 21 enhances the resolution of at least one or more of the plurality of frame images to the high resolution and generates the high definition still image 50 or the high definition dynamic image 60 as the secondary medical image (image generator).

According to the above, there is no need to perform radiation imaging to obtain the high definition medical image separately from the radiation imaging for the medical dynamic image 40. Therefore, it is possible to suppress the dose of radiation the patient receives in the examination and the burden on the patient can be reduced. Moreover, the number of times the radiation imaging is performed and the duration time in the examination can be reduced. Therefore, the efficiency of the examination can be enhanced.

The secondary medical image obtained by enhancing the resolution to a high resolution is not the actual image obtained by imaging the patient. Therefore, if such image is used to be interpreted for diagnosis, there is a possibility that medical problems such as erroneous diagnosis may occur.

Specifically, the secondary medical image obtained by enhancing the resolution to a high resolution is easily mistakenly used when the radiation image is interpreted. The reason is because the secondary medical image generated by enhancing the resolution cannot be discriminated at a glance from the medical image originally imaged at a high resolution (for example, a high definition still image obtained by X-ray simple imaging). This is because the purpose of the process of enhancing the resolution to the high resolution is to make the image closer to a high definition image obtained by X-ray simple imaging by enhancing the resolution. Therefore, as the technique of the process to enhance the resolution to the high resolution becomes developed, the discrimination from the image imaged at a high resolution becomes difficult, and this leads to mistaken use. The situation is different from other image processes such as a bone suppression process in which the bone portion becomes unnoticeable.

According to the present embodiment, the recording process is performed on the secondary medical image generated by enhancing the resolution to the high resolution, and the display of the annotation mark 80 is performed according to the recording process. Therefore, it is possible to suppress medical problems occurring due to mistakenly using and interpreting the secondary medical image in which the resolution is enhanced to the high resolution.

The secondary medical image is a high definition still image 50 which can be obtained by enhancing the resolution of one or more of the frame images among the plurality of frame images. With this, the high definition still image 50 with the higher resolution than the frame images of the originally generated medical dynamic image 40 can be obtained.

The controller 21 receives an instruction from the user specifying one or more of the frame images (receiver), enhances the resolution of one or more of the specified frame images, and generates the high definition still image 50 (image generator). With this, the resolution of the desired frame image can be enhanced to the high resolution and used.

The controller 21 enhances the resolution of one or more of the frame images corresponding to the specific timing determined by cyclic movement of the subject and generates the high definition still image 50 (image generator). Therefore, it is possible to obtain the high definition still image 50 in which the resolution of the suitable representative image in the medical dynamic image 40 is enhanced to the high resolution without the user specifying the frame image.

The controller 21 displays on the display 34 the high definition still image 50 as the secondary medical image together with the medical dynamic image 40 (display controller). With this, the user is able to confirm together with the medical dynamic image 40 that has the low resolution the high definition still image 50 that has the high resolution and that corresponds with one or more of the frames of the medical dynamic image 40.

The secondary medical image is the high definition dynamic image 60 including two or more high definition frame images obtained by enhancing the resolution of two or more of the plurality of frame images to the high resolution. With this, the high definition dynamic image 60 with a higher resolution than the originally generated medical dynamic image 40 can be obtained.

The secondary medical image includes the high definition still image 50 obtained by enhancing the resolution of one or more of the frame images among the plurality of frame images and the high definition dynamic image 60 including the two or more high definition frame images obtained by enhancing the resolution of two or more images among the plurality of medical images. The controller 21 displays on the display 34 the high definition still image 50 together with the high definition dynamic image 60. With this, the high definition dynamic image 60 with the higher resolution than the originally generated medical dynamic image 40 can be confirmed together with the high definition still image 50 with the high resolution.

The medical image management apparatus 2 includes a storage 22 which stores image data of the secondary medical image. The controller 21 deletes from the storage 22 the image data of the secondary medical image in which the predetermined storage term elapsed (image deleter). With this, it is possible to avoid the problems such as the storage capacity of the storage 22 becoming insufficient and not being able to store the new image data.

The program 223 regarding the present embodiment allows the controller 21 as the computer provided in the medical image management apparatus 2 as the moving image processing apparatus to function as an image generator which generates the high definition still image 50 and the high definition dynamic image 60 as the secondary medical image based on at least one or more of the plurality of frame images included in the medical dynamic image 40 and the recorder which executes the recording process which performs the recording showing that the secondary medical image is generated secondarily from the existing medical dynamic image 40. According to such program, it is possible to improve the efficiency of the examination and the burden on the patient (received dose, etc.) can be decreased. Further, when the recording process is performed on the secondary medical image, the display of the annotation mark 80 may be performed according to the recording process. With this, it is possible to suppress medical problems occurring due to erroneously using the secondary medical image to be interpreted in the diagnosis.

The description of the embodiments described above is an example of the dynamic image processing analysis according to the present embodiment, and the present embodiment is not limited to the above. The detailed configuration and the detailed operation of each unit included in the apparatus can be suitably changed without leaving the scope of the present invention.

For example, the annotation mark 80 is shown as the note mark according to the present embodiment, but the note mark may be any mark which shows that the high definition still image 50 and the high definition dynamic image 60 which are secondary medical images are generated secondarily from the existing medical dynamic image. For example, the note mark can be letters displayed in the image information 71 of the information display screen 70.

The high definition still image 50, the high definition dynamic image 60, and the thumbnail image 74 are shown as the secondary medical image, but the present embodiment is not limited to the above. Any medical image generated based on the frame image of the medical dynamic image 40 may be the secondary medical image. For example, the image obtained by performing the image process of the bone suppressing process on the frame image corresponds to the secondary medical image.

The above embodiment describes displaying the medical dynamic image 40 and the high definition still image 50 aligned in the same information display screen 70 (FIG. 6), and the high definition dynamic image 60 and the high definition still image 50 aligned in the same information display screen 70 (FIG. 7), but the present embodiment is not limited to the above. When the display 34 includes a plurality of monitors 341, the images can be displayed in separate monitors 341.

The medical image management apparatus 2 is provided with an operator and a display. When the user is able to directly operate the medical image management apparatus 2, the medical image management apparatus 2 may receive the user operation. In this case, the contents displayed on the display 34 of the medical image display apparatus 3 according to the above-described embodiment are displayed on the display of the medical image management apparatus 2.

According to the above-described embodiment, the controller 21 of the medical image management apparatus 2 functions as the image generator, recorder, image controller, receiver, and image deleter. Instead of the above, the controller 31 of the medical image display apparatus 3 may perform the above functions. In this case, the medical image display apparatus 3 corresponds to the "dynamic image processing apparatus".

The medical image display apparatus 3 may be the console used to control the medical image imaging apparatus 1.

According to the present embodiment, the database 221 and the image storage region 222 are provided in the storage 22 of the medical image management apparatus 2, but the present embodiment is not limited to the above. For example, a database 221 can be provided in a database server, etc. outside of the medical image management apparatus 2, and the necessary data can be obtained from the database server each time. Similarly, the image data of the radiation image may be stored in the storage apparatus outside of the medical image management apparatus 2, and the necessary image data can be obtained each time from the storage apparatus.

According to the above described embodiment, the medical dynamic image 40 includes the frame images of the radiation image generated in response to irradiation of radiation to the subject. However, the present invention is not limited to the above, and the medical dynamic image 40 may include frame images imaged by other methods.

According to the above description, the storage 22 or the ROM is used as the computer-readable medium storing the program to execute various processes, but the present embodiment is not limited to the above examples. As other computer readable media, a nonvolatile memory such as a flash memory, a portable storage medium such as a CD-ROM can be applied. A carrier wave can be applied as the media providing the data of the program through the communication lines.

Although embodiments of the present invention have been described and illustrated in detail, the disclosed embodiments are made for purposes of illustration and example only and not limitation. The scope of the present invention should be interpreted by terms of the appended claims.

What is claimed is:

1. A dynamic image processing apparatus which processes image data of a medical dynamic image that includes a plurality of frame images obtained from successively imaging a subject and that shows a dynamic state of the subject, the apparatus comprising:
   a hardware processor, wherein
   the hardware processor enhances resolution of at least one or more of the plurality of frame images included in the medical dynamic image to a high resolution and generates a secondary medical image, and
   the hardware processor executes a recording process in which a record is kept to show that the secondary medical image is generated secondarily from the existing medical dynamic image, wherein
   a frame image used for generating the secondary medical image among the plurality of frame images and the secondary medical image are images having different resolutions.

2. The dynamic image processing apparatus according to claim 1, wherein each of the plurality of frame images is an image that is generated according to irradiation of radiation on the subject.

3. The dynamic image processing apparatus according to claim 1, wherein,
   the hardware processor controls a display to display the secondary medical image,
   based on a result of the recording process, the hardware processor controls the display to display on the display together with the secondary medical image a note mark showing that the secondary medical image is secondarily generated from the existing medical dynamic image.

4. The dynamic image processing apparatus according to claim 3, wherein, in the recording process, the hardware processor updates image data of the secondary medical image to image data of an image including the secondary medical image and the note mark, and based on the updated image data, the hardware processor controls the display to display on the display the secondary medical image and the note mark.

5. The dynamic image processing apparatus according to claim 3, wherein, in the recording process, the hardware processor keeps the record in supplementary data of the image data of the secondary medical image, and based on the supplementary data in which the record is kept, the hardware processor controls the display to display on the display the note mark together with the secondary medical image.

6. The dynamic image processing apparatus according to claim 3, wherein, the hardware processor controls the display to display on the display the note mark together with a thumbnail image when a thumbnail image of the secondary medical image is displayed on the display.

7. The dynamic image processing apparatus according to claim 1, wherein the secondary medical image is a high definition still image obtained by enhancing the resolution of one or more of the frame images of the plurality of frame images to a high resolution.

8. The dynamic image processing apparatus according to claim 7, wherein, the hardware processor receives an input by the user specifying one or more of the frame images, and the hardware processor enhances the resolution of one or more of the specified frame images to the high resolution and generates the high definition still image.

9. The dynamic image processing apparatus according to claim 7, wherein, the hardware processor enhances to the high resolution the resolution of one or more of the frame images corresponding to a specific timing determined by a cyclic movement of the subject and generates the high definition still image.

10. The dynamic image processing apparatus according to claim 7, wherein, the hardware processor controls the display to display the secondary medical image, and the hardware processor controls the display to display the high definition still image as the secondary medical image together with the medical dynamic image.

11. The dynamic image processing apparatus according to claim 1, wherein, the secondary medical image is a high definition dynamic image including two or more high definition frame images obtained by enhancing the resolution of two or more of the plurality of frame images to the high resolution.

12. The dynamic image processing apparatus according to claim 1, wherein, the hardware processor controls the display to display the secondary medical image, the secondary medical image includes a high definition still image obtained by enhancing the resolution of one or more of the plurality of frame images to the high resolution, and the high definition dynamic image including two or more high definition frame images obtained by enhancing the resolution of two or more frame images among the plurality of medical images, and the hardware processor controls the display to display both the high definition still image and the high definition dynamic image.

13. The dynamic image processing apparatus according to claim 1, further comprising a storage that stores the image data of the secondary medical image, wherein, the hardware processor deletes from the storage the image data of the secondary medical image in which a predetermined storage time elapsed.

14. A non-transitory computer-readable storage medium storing a program causing a computer provided in a dynamic image processing apparatus that processes image data of a medical dynamic image that includes a plurality of frame images obtained by successively imaging a subject and that shows a dynamic state of the subject to perform the following:

generating a secondary medical image by enhancing a resolution of at least one or more of the plurality of frame images included in the medical dynamic image, and executing a recording process to keep a record showing that the secondary medical image is generated secondarily from the existing medical dynamic image, wherein a frame image used for generating the secondary medical image among the plurality of frame images and the secondary medical image are images having different resolutions.

* * * * *